US010190171B2

(12) United States Patent
Board et al.

(10) Patent No.: US 10,190,171 B2
(45) Date of Patent: Jan. 29, 2019

(54) POLYNUCLEOTIDE PRIMERS FOR DETECTING PIK3CA MUTATIONS

(71) Applicant: QIAGEN MANCHESTER LIMITED, Manchester (GB)

(72) Inventors: Ruth Board, Manchester (GB); Jennifer Haworth, Manchester (GB); Paul Francis Ravetto, Manchester (GB); Nicola Jo Thelwell, Manchester (GB); David Whitcombe, Manchester (GB)

(73) Assignee: QIAGEN MANCHESTER LIMITED, Manchester (GB)

( * ) Notice: Subject to any disclaimer, the term of this patent is extended or adjusted under 35 U.S.C. 154(b) by 552 days.

(21) Appl. No.: 14/858,196

(22) Filed: Sep. 18, 2015

(65) Prior Publication Data
US 2016/0040255 A1 Feb. 11, 2016

Related U.S. Application Data

(62) Division of application No. 14/062,163, filed on Oct. 24, 2013, now Pat. No. 9,863,003, which is a division of application No. 12/680,621, filed as application No. PCT/GB2008/003306 on Sep. 29, 2008, now Pat. No. 8,901,285.

(30) Foreign Application Priority Data

Sep. 28, 2007 (GB) .................................. 0719034.1

(51) Int. Cl.
*C12Q 1/68* (2018.01)
*C12Q 1/6886* (2018.01)
*C12Q 1/6844* (2018.01)
*C12Q 1/6883* (2018.01)

(52) U.S. Cl.
CPC ......... *C12Q 1/6886* (2013.01); *C12Q 1/6844* (2013.01); *C12Q 1/6883* (2013.01); *C12Q 2600/156* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 5,210,015 A | 5/1993 | Gelfand et al. | |
| 5,824,492 A * | 10/1998 | Hiles ...................... | C07K 16/40 435/15 |
| 5,846,824 A | 12/1998 | Hiles et al. | |
| 5,847,972 A | 12/1998 | Eick et al. | |
| 5,955,277 A | 9/1999 | Hansen et al. | |
| 5,994,076 A | 11/1999 | Chenchik et al. | |
| 6,133,419 A | 10/2000 | Braselmann | |
| 6,274,237 B1 | 8/2001 | Nakajima et al. | |
| 6,277,563 B1 | 8/2001 | Shayesteh et al. | |
| 6,291,220 B1 | 9/2001 | Williams et al. | |
| 6,300,111 B1 | 10/2001 | Klippel et al. | |
| 6,326,145 B1 * | 12/2001 | Whitcombe ......... | C12Q 1/6818 435/5 |
| 6,537,751 B1 | 3/2003 | Cohen et al. | |
| 6,812,339 B1 | 11/2004 | Venter et al. | |
| 7,122,373 B1 | 10/2006 | Williams et al. | |
| 7,422,849 B1 | 9/2008 | Hiles et al. | |
| 8,901,285 B2 | 12/2014 | Board et al. | |
| 9,863,003 B2 | 1/2018 | Board et al. | |
| 2003/0182669 A1 | 9/2003 | Rockman et al. | |
| 2004/0110197 A1 | 6/2004 | Skinner et al. | |
| 2004/0132050 A1 | 7/2004 | Monforte | |
| 2004/0181048 A1 | 9/2004 | Wang | |
| 2005/0227917 A1 | 10/2005 | Williams et al. | |
| 2005/0287559 A1 | 12/2005 | Cargill et al. | |
| 2006/0026702 A1 | 2/2006 | Rockman et al. | |
| 2006/0211036 A1 | 9/2006 | Chou et al. | |
| 2007/0048754 A1 | 3/2007 | Freeman et al. | |
| 2007/0054278 A1 | 3/2007 | Cargill | |
| 2008/0145852 A1 | 6/2008 | Shuber | |
| 2009/0192110 A1 | 7/2009 | Hedtjarn | |
| 2009/0208505 A1 | 8/2009 | Samuels et al. | |
| 2014/0141425 A1 | 5/2014 | Board et al. | |
| 2016/0032408 A1 | 2/2016 | Board et al. | |

FOREIGN PATENT DOCUMENTS

| | | |
|---|---|---|
| AU | 2008303400 A1 | 4/2009 |
| BR | PI0817444 A2 | 6/2015 |
| CA | 2700710 A1 | 4/2009 |
| CN | 102119222 A | 7/2011 |

(Continued)

OTHER PUBLICATIONS

Lowe et al. A computer program for selection of oligonucleotide primers for polymerase chain reactions. Nucleic Acids research, vol. 18(7), p. 1757-1761, 1990.*
Response to Non-Final Office Action filed on Feb. 9, 2016 with the U.S. Patent and Trademark Office for U.S. Appl. No. 14/062,163, filed Oct. 24, 2013 and published as US 2014-0141425 A1, dated May 22, 2014 (Inventor-Ruth Board et al.; Applicant-Qiagen GmbH;) (13 pages).
Final Office Action was dated Apr. 18, 2016 by the U.S. Patent and Trademark Office for U.S. Appl. No. 14/062,163, filed Oct. 24, 2013 and published as US 20140-141425 A1, dated May 22, 2014 (Inventor-Ruth Board et al.; Applicant- Qiagen GmbH;) (7 pages).

(Continued)

*Primary Examiner* — Suryaprabha Chunduru
(74) *Attorney, Agent, or Firm* — Ballard Spahr LLP

(57) ABSTRACT

A polynucleotide comprising at least the final six nucleotides of one of the following primer sequences, or a sequence complementary thereto: SEQ. ID NOS. 3 to 16, 18, 20 to 33, 35 or 37 to 39. A method of detecting the presence or absence of a mutation in the PIK3CA gene, wherein the mutation is one of H1047R, H1047L, E542K and E545K, and preferably ARMS primers are combined with Scorpion primers.

15 Claims, 1 Drawing Sheet
Specification includes a Sequence Listing.

(56) References Cited

FOREIGN PATENT DOCUMENTS

| CN | 103695558 A | 4/2014 | |
|---|---|---|---|
| CN | 103834724 A | 6/2014 | |
| CN | 103952466 A | 7/2014 | |
| EP | 0332435 A2 | 9/1989 | |
| EP | 2205760 A2 | 7/2010 | |
| EP | 2236627 A1 | 10/2010 | |
| EP | 2239341 A1 | 10/2010 | |
| EP | 2505671 A1 | 10/2012 | |
| EP | 2505672 A1 | 10/2012 | |
| EP | 2505673 A1 | 10/2012 | |
| EP | 2508624 A1 | 10/2012 | |
| ES | 2531055 T3 | 3/2015 | |
| ES | 2531994 T3 | 3/2015 | |
| ES | 2532141 T3 | 3/2015 | |
| ES | 2532225 T3 | 3/2015 | |
| GB | 2453173 A | 4/2009 | |
| JP | 2002-360120 A | 12/2002 | |
| JP | 2010-539920 A | 12/2010 | |
| KR | 20100101070 A | 9/2010 | |
| KR | 20150038659 A | 4/2015 | |
| KR | 20150038660 A | 4/2015 | |
| KR | 20150038661 A | 4/2015 | |
| MX | 20100003486 | 8/2010 | |
| RU | 2010116772 | 9/2008 | |
| WO | WO-1999/066071 A1 | 12/1999 | |
| WO | WO-2001/030362 A2 | 5/2001 | |
| WO | WO-2003/025175 A2 | 3/2003 | |
| WO | WO-2004/048511 A2 | 6/2004 | |
| WO | WO-2005/091849 A2 | 10/2005 | |
| WO | WO-2005/116265 A2 | 12/2005 | |
| WO | WO-2006/091899 A2 | 8/2006 | |
| WO | WO-2007/050465 A2 | 5/2007 | |
| WO | WO-2007050465 A2 * | 5/2007 | ........... C12Q 1/6858 |
| WO | WO-2007/106407 A2 | 9/2007 | |
| WO | WO-2009/040557 A2 | 4/2009 | |

OTHER PUBLICATIONS

Response After Final Office Action and Request for Continued Examination filed on Oct. 14, 2016 with the U.S. Patent and Trademark Office for U.S. Appl. No. 14/062,163, filed Oct. 24, 2013 and published as US 2014-0141425 A1, dated May 22, 2014 (Inventor-Ruth Board et al.; Applicant- Qiagen GmbH;) (20 pages).
Non-Final Office Action dated Jan. 4, 2017 by the U.S. Patent and Trademark Office for U.S. Appl. No. 14/062,163, filed Oct. 24, 2013 and published as US 2014-0141425 A1, dated May 22, 2014 (Inventor-Ruth Board et al.; Applicant- Qiagen GmbH;) (11 pages).
Response to Non-Final Office Action dated Apr. 3, 2017 by the U.S. Patent and Trademark Office for U.S. Appl. No. 14/062,163, filed Oct. 24, 2013 and published as US 2014-0141425 A1, dated May 22, 2014 (Inventor-Ruth Board et al.; Applicant- Qiagen GmbH;) (20 pages).
Final Office Action dated Jun. 12, 2017 by the U.S. Patent and Trademark Office for U.S. Appl. No. 14/062,163, filed Oct. 24, 2013 and published as US 2014-0141425 A1, dated May 22, 2014 (Inventor-Ruth Board et al.; Applicant- Qiagen GmbH;) (9 pages).
Altschul, S. et al., Gapped Blast and PSSI-Blast: A New Generation of Protein Database Search Programs, Nucleic Acids Res, 25(17): 3389-402 (1997).
Bachman, K. et al., the PIK3CA Gene is Mutated with High Frequency in Human Breast Cancers, Cancer Biol Ther, 3(8): 772-5 (2004).
Board, R.E. et al., Multiplexed Assays for Detection of Mutations in PIK3CA, Clin Chem, 54(4): 757-60 (2008).
Broderick, D.K. et al., Mutations of PIK3CA in Anaplastic Oligodendrogliomas, High-Grade Asterocytomas and Medulloblastomas, Cancer Res, 64: 5048-50 (2004).
Byun, D.S. et al., Frequent Monoallelic Deletion of PTEN and Its Reciprocal Association with PIK3CA Amplification in Gastric Carcinoma, Intl J Cancer, 104: 318-27 (2003).

Callaghan, K.K. et al., Characterization of K-RAS Mutations by a Non-Gel-Based Procedure Combining Arms Primer Extension and Taqman, Am J Human Genetics, 61(4): A62 (1997).
Campbell, I.G. et al., Mutation of the PIK3CA Gene in Ovarian and Breast Cancer, Cancer Res, 64(21): 7678-81 (2004).
Database EMBL (Online), Sequence 5111 from Patent WO 03/025175, XP002508215 (Retrieved from EBI Accession No. EMBL:AX733477 on May 8, 2003) (1 page).
Database Geneseq (Online), Viral Regulatory miRNA Seq ID No. 399147, (Retrieved from EBI Accession No. GSN:AJL46829 on Dec. 28, 2007).
Database Geneseq (Online), Human Mitochondrial DNA Deleted Sequence Probe #5 (Retrieved from EBI Accession No. GSN:ABZ69094 on Aug. 11, 2003).
Database Geneseq (Online), Sequence 77548 from Patent WO 2005/116265 (Retrieved from EBI Accession No. EMBL:HA856363 on Jun. 5, 2009).
Database Geneseq (Online), (Retrieved from EBI Accession No. GSN: AEE69215 on Feb. 23, 2006).
Database Geneseq (Online), Cyclin H Ribozyme Binding Site Seq ID No. 2948, (Retrieved from EBI Accession No. GSN:AAH60525 on Sep. 10, 2001).
Gallia, G.L. et al., PIK3CA gene mutations in pediatric and adult glioblastoma multiform. Mol Cancer Res, 4(10): 709-14 (2006).
GenBank Accession No. NM_006218 Version No. NM_006218.2 GI: 54792081.
Gymnopoulos, M. et al., Rare Cancer-Specific Mutation in PIK3CA Show Gain of Function, Proc Natl Acad Sci USA, 104(13): 5569-74 (2007).
Hafner, C. et al., Oncogenic PIK3CA Mutations Occur in Epidermal Nevi and Seborrheic Keratoses with a Characteristic Mutation Pattern, Proc Natl Acad Sci USA, 104(33): 13450-4 (2007).
Hartman, C. et al., PIK3CA Mutations in Glioblasctoma Multiforme, Acta Neuropathol, 109: 639-42 (2005).
Higuchi et al., A General Method of in Vitro Preparation and Specific Mutagenesis of DNA Fragments: Study of Protein and DNA Interactions, Nucleic Acids Res, 16(15): 7351-67 (1988).
Horike, A. et al., Detection of Epidermal Growth Factor Receptor Mutation in Transbronchial Needle Aspirates of Non-Small Cell Lung Cancer, Chest, 131(6): 1628-34 (2007).
Hurst, C.D. et al., A Snapshot Assay for the Rapid and Simple Detection of Four Common Hotspot Codon Mutations in the PIK3CA Gene, BMC Research Notes, Published online Apr. 29, 2009, doi: 10.1186/1756-0500-2-66.
Kalinsky, K. et al., PIK3CA Mutation Associates with Improved Outcome in Breast Cancer, Clin Cancer Res, 15(16): 5049-59 (2009).
Kawano, O. et al., PIK3CA Mutation Status in Japanese Lung Cancer Patients, Lung Cancer, 54: 209-15 (2006).
Kita, D. et al., PIK3CA Alterations in Primary (de novo) and Secondary Glioblastomas, Acta Neuropthol, 113: 295-302 (2007).
Knobbe, C.B. et al., Genetic Alteration and Aberrant Expression of Genes Related to the Phosphatidyl-Inosilol-3'-Kinase/Protein Kinase B (Akt) Signal Transduction Pathway in Glioblastomas, Brain Pathol, 13(4): 507-18 (2003).
Kotayama, S. et al. Antisense transcription in mammalian transcriptions. Science, vol. 309, p. 1564-1566, 2005.
Lee, J.W. et al., PIK3CA Gene is Frequently Mutated in Breast Carcinomas and Hepatocellular Carcinomas, Oncogene, 24(8): 1477-80 (2005).
Levine et al., Frequent Mutation of the PIK3CA Gene in Ovarian and Breast Cancers, Clin Cancer Res, 11(8): 2875-8 (2005).
Liedtke, C. et al., PIK3CA-Activating Mutations and Chemotherapy Sensitivity in Stage II-III Breast Cancer, Breast Cancer Res, 10(2) (2008).
Lowe et al., A Computer Program for Selection of Oligonucleotide Primers for Polymerase Chain Reactions, Nucleic Acids Res, 18(7): 1757-61.
Mizoguchi, M. et al., Genetic Alterations of Phsophoinositide 3-Kinase Subunit Genes in Human Glioblastomas, Brain Pathol, 14(4): 372-7 (2004).
Muller, C.I. et al., Rare Mutations of the PIK3CA Gene in Hematologic Malignancies, Blood, 104(11): 172B (2004).

(56) References Cited

OTHER PUBLICATIONS

Muller, C.I. et al., Rare Mutations of the PIK3CA Gene in Malignancies of the Hematopoietic System as well as Endometrium, Ovary, Prostatem and Osteosarcomas, and Discovery of a PIK3CA Psuedogene, Leukemia Res, 31: 27-32 (2007).

Newton et al., Analysis of Any Point Mutation in DNA: The Amplification Refractory Mutation System (ARMS), Nucleic Acids Res, 17(7): 2503-16 (1989).

Omholt, K. et al., Mutations of PIK3CA Are Rare in Cutaneous Melanoma, Melanoma Res, 16(2): 197-200 (2006).

Qiu, W. et al., Novel Mutant-Enriched Sequencing Identified High Frequency of PIK3CA Mutations in Pharyngeal Cancer, Intl J Cancer, 122: 1189-94 (2008).

Qiu, W. et al., PIK3CA Mutations in Head and Neck Squamous Cell Carcinoma, Clin Cancer Res, 12(5): 1441-6 (2006).

Samuels, Y. et al., High Frequency of Mutations of the PIK3CA Gene in Human Cancers, Science, 304(5670): 554 (2004).

Santarpia, M. et al., PIK3CA Mutations in Breast Cancer: A Potential Predictive Marker, J Clin Oncol, 24(18S): 639 (2006).

Singh, B. et al., P53 Regulates Cell Survival by Inhibiting PIK3CA in Squamous Cell Carcinomas, Genes Dev, 16(8): 984-93 (2002).

Smith et al., CXCL 12 Activation of CXCR4 Regulates Mucosal Host Defense Through Stimulation of Epithelial Cell Migration and Promotion of Intestinal Barrier Integrity, Am J Physiol Castrointest Liver Physiol, 288(2): G316-26 (2005).

Stratagene Catalog, Gene Characterization Kits, p. 39 (1988).

Tanaka, Y. et al., Absence of PIK3CA Hotspot Mutations in Hepatocellular Carcinoma in Japanese Patients, Oncogene, 25: 2950-2 (2006).

Thelwell et al., Mode of Action and Application of Scorpion Primers to Mutation Detection, Nucleic Acids Res, 28(19): 3752-61 (2000).

Velasco, A et al., PIK3CA Gene Mutations Endometrial Carcinoma: Correlation with PTEN and K-RAS Alterations, Human Pathol, 37: 1465-72 (2006).

Velho, S. et al., The Prevalence of PIK3CA Mutations in Gastric and Colon Cancer, Eur J Cancer, 41(11): 1649-54 (2005).

Wang et al., PIK3CA Mutations in Advanced Ovarian Carcinomas, Hum Mutat, 25(3): 322 (2005).

Weir, B. et al., Somatic Alterations in the Human Cancer Genome, Cancer Cell, 6(5): 433-8 (2004).

Whitcombe, D. et al., Detection of PCR Products Using Self-Probing Amplicons and Fluorescence, Nat Biotechnol, 17(8): 804-7 (1999).

Wu, G.et al., Somatic Mutation and Gain of Copy Number of PIK3CA in Human Breast Cancer, Breast Cancer Res, 7(5): R609-16 (2005).

European Search Report dated Aug. 26, 2010 for European Patent Application No. 08 806 456.3, which was filed on Sep. 29, 2008 and published as EP 2205760 dated Jul. 14, 2010.

Extended European Search Report dated Sep. 2, 2010 for European Patent Application No. 10158519.8, which was filed on Sep. 29, 2008 and published as EP 2236627 dated Oct. 16, 2010.

Extended European Search Report dated Sep. 2, 2010 for European Patent Application No. 10158523.0, which was filed on Sep. 29, 2008 and published as EP 2239341 dated Oct. 13, 2010.

Examination Report dated Aug. 24, 2012 for EP 10158523.0, which was filed on Sep. 29, 2008 and published as EP 2239341 dated Oct. 13, 2010.

European Search Report and Written Opinion dated Sep. 4, 2012 by the European Patent Office for European Patent Application No. 12169586.0, which was filed on Sep. 29, 2008 and published as EP 2505671 dated Oct. 3, 2012 (Inventor—Board et al.; Applicant—Qiagen Manchester Ltd.) (12 pages).

European Search Report and Written Opinion dated Sep. 4, 2012 by the European Patent Office for European Patent Application No. 12169594.4, which was filed on Sep. 29, 2008 and published as EP 2505672 dated Oct. 3, 2012 (Inventor—Board et al.; Applicant—Qiagen Manchester Ltd.) (12 pages).

European Search Report and Written Opinion dated Sep. 4, 2012 by the European Patent Office for European Patent Application No. 12169599.3, which was filed on Sep. 29, 2008 and published as EP 2505673 dated Oct. 3, 2012 (Inventor—Board et al.; Applicant—Qiagen Manchester Ltd.) (12 pages).

Non-Final Office Action dated Jan. 10, 2013 by the U.S. Patent and Trademark Office for U.S. Appl. No. 12/680,621, filed Oct. 19, 2010 and now U.S. Pat. No. 8,901,285 dated Dec. 2, 2014 (Inventor—Board et al.; Applicant—Qiagen Manchester Ltd.;).

Advisory Action dated Jan. 10, 2013 by the U.S. Patent and Trademark Office for U.S. Appl. No. 12/680,621, filed Oct. 19, 2010 and now U.S. Pat. No. 8,901,285 dated Dec. 2, 2014 (Inventor—Board et al.; Applicant—Qiagen Manchester Ltd.;).

Non-Final Office Action dated Oct. 7, 2013 by the U.S. Patent and Trademark Office for U.S. Appl. No. 12/680,621, filed Oct. 19, 2010 and now U.S. Pat. No. 8,901,285 dated Dec. 2, 2014 (Inventor—Board et al.; Applicant—Qiagen Manchester Ltd.;).

Final Office Action dated Feb. 19, 2014 by the U.S. Patent and Trademark Office for U.S. Appl. No. 12/680,621, filed Oct. 19, 2010 and now U.S. Pat. No. 8,901,285 dated Dec. 2, 2014 (Inventor—Board et al.; Applicant—Qiagen Manchester Ltd.;).

Advisory Action dated Jun. 25, 2014by the U.S. Patent and Trademark Office for U.S. Appl. No. 12/680,621, filed Oct. 19, 2010 and now U.S. Pat. No. 8,901,285 dated Dec. 2, 2014 (Inventor—Board et al.; Applicant—Qiagen Manchester Ltd.;).

Notice of Allowance dated Aug. 14, 2014 by the U.S. Patent and Trademark Office for U.S. Appl. No. 12/680,621, filed Oct. 19, 2010 and now U.S. Pat. No. 8,901,285 dated Dec. 2, 2014 (Inventor—Board et al.; Applicant—Qiagen Manchester Ltd.;).

Issue Notification issued on Dec. 2, 2014 by the U.S. Patent and Trademark Office for U.S. Appl. No. 12/680,621, filed Oct. 19, 2010 and now U.S. Pat. No. 8,901,285 on Dec. 2, 2014 (Inventor—Board et al.; Applicant—Qiagen Manchester Ltd.;) (1 page).

Restriction Requirement dated Aug. 13, 2015 by the U.S. Patent and Trademark Office for U.S. Appl. No. 14/062,163, filed Oct. 24, 2013 and published as US 2014/0141425 dated May 22, 2015 (Inventor—Board et al.; Applicant—Qiagen Manchester Ltd.;) (6 pages).

Response to Restriction Requirement filed on Sep. 17, 2015 with the U.S. Patent and Trademark Office for U.S. Appl. No. 14/062,163, filed Oct. 24, 2013 and published as US 2014/0141425 dated May 22, 2015 (Inventor—Board et al.; Applicant—Qiagen Manchester Ltd.;) (6 pages).

Non-Final Office Action dated Oct. 9, 2015 by the U.S. Patent and Trademark Office for U.S. Appl. No. 14/062,163, filed Oct. 24, 2013 and published as US 2014/0141425 dated May 22, 2015 (Inventor—Board et al.; Applicant—Qiagen Manchester Ltd.;) (15 pages).

Shayesteh, L. et al. PIK3CA is implicated as an oncogene in ovarian cancer. Nature Genetics, vol. 21, p. 99-102, 1999.

Response to Final Rejection dated Sep. 1, 2017 to the USPTO for U.S. Appl. No. 14/062,163, filed Oct. 24, 2013, and now U.S. Pat. No. 9,863,003 dated Jan. 9, 2018 (Inventor- Ruth Board, et al.) (5 pages).

Notice of Allowance dated Sep. 20, 2017 by the USPTO for U.S. Appl. No. 14/062,163, filed Oct. 24, 2013, and now U.S. Pat. No. 9,863,003 dated Jan. 9, 2018 (Inventor- Ruth Board, et al.) (8 pages).

Issue Notification was issued on Dec. 20, 2017 by the USPTO for U.S. Appl. No. 14/062,163, filed Oct. 24, 2013, and now U.S. Pat. No. 9,863,003 dated Jan. 9, 2018 (Inventor- Ruth Board, et al.) (1 page).

Requirement for Restriction/ Election dated Jan. 23, 2018 by the USPTO for U.S. Appl. No. 14/858,188, filed Sep. 18, 2015 and published as US 2016/0032408 A1 dated Feb. 4, 2016 (Inventor- Ruth Board, et al.) (6 pages).

Response to Requirement for Restriction/ Election dated Feb. 20, 2018 by the USPTO for U.S. Appl. No. 14/858,188, filed Sep. 18, 2015 and published as US 2016/0032408 A1 dated Feb. 4, 2016 (Inventor- Ruth Board, et al.) (9 pages).

Non Final dated Apr. 12, 2018 by the USPTO for U.S. Appl. No. 14/858,188, filed Sep. 18, 2015 and published as US 2016/0032408 A1 dated Feb. 4, 2016 (Inventor- Ruth Board, et al.) (6 pages).

\* cited by examiner

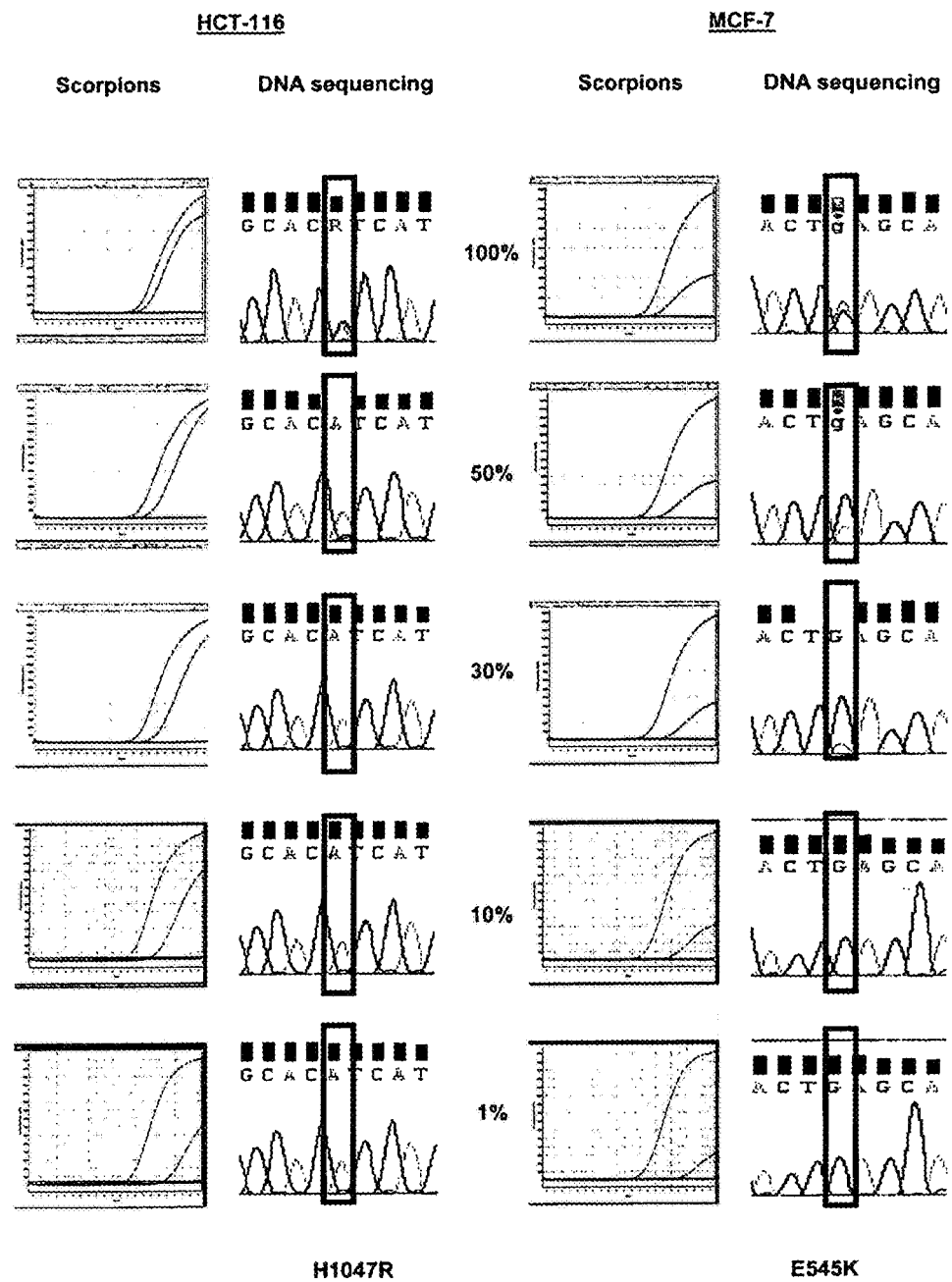

POLYNUCLEOTIDE PRIMERS FOR DETECTING PIK3CA MUTATIONS

CROSS-REFERENCE TO RELATED APPLICATIONS

The present application is a divisional application of U.S. application Ser. No. 14/062,163, filed Oct. 24, 2013, which is a divisional application of U.S. application Ser. No. 12/680,621, filed Oct. 19, 2010, which is a National Stage Entry of Serial No. PCT/GB2008/003306, filed Sep. 29, 2008, which claims priority to Great Britain Application No. 0719034.1, filed Sep. 28, 2007, the full disclosures of which are hereby incorporated herein by their reference.

REFERENCE TO SEQUENCE LISTING

The Sequence Listing submitted Sep. 17, 2015 as a text file named "17104_0031U4_Sequence_Listing.txt," created on Sep. 16, 2015, and having a size of 8,132 bytes is hereby incorporated by reference pursuant to 37 C.F.R. § 1.52(e)(5).

TECHNICAL FIELD

The present invention relates to a polynucleotide, a kit comprising a polynucleotide and a method for detecting the presence or absence of mutations in a gene.

BACKGROUND ART

Phosphatidylinositol 3-Kinases (PI3K) are a large family of lipid kinases involved in cell signaling. The PBK-AKT pathway is activated in a number of tumour types, resulting in abnormalities of cell growth, proliferation and survival (add ref of 1 recent review). Recently, mutations in the catalytic subunit of the class 1A PI3K (PIK3CA) have been identified in human cancers[1]. The precise role of these mutations in carcinogenesis is still to be clearly defined but with ongoing development of a number of targeted PI3K inhibitors, detection of mutations will become increasingly important for patient selection. Technical challenges in the detection of such mutations result from the limitations of tumour biopsies that may only contain small quantities of the mutated sequences. Furthermore, DNA extracted from paraffin embedded tissue is often degraded and of poor quality. The minimum level of mutant DNA required for detection by sequencing is 15-25% and so there is a pressing need for development of sensitive assays able to detect small amounts of mutated alleles in a heterogenous sample and the products necessary for carrying out the assays.

The present invention seeks to address this need.

DISCLOSURE OF THE INVENTION

The present invention provides sensitive and robust tests for tumour-borne PIK3CA mutations.

According to one aspect of the present invention, there is provided a polynucleotide comprising at least the final six nucleotides of one of the following primer sequences, or a sequence complementary thereto; SEQ. ID NOS. 3 to 16, 18, 20 to 33, 35 or 37 to 39. That is, the polynucleotide comprises at least the six nucleotides at the 3' end of one of the following primer sequences, or a sequence complementary thereto: SEQ. ID NOS. 3 to 16, 18, 20 to 33, 35 or 37 to 39.

Preferably, the polynucleotide comprises at least 75% of the 8, 10, 12, 14, 16, 17, 18 or 20 nucleotides at the 3' end, or the entirety, of one of the following primer sequences, a sequence complementary thereto, or a sequence having 80%, 90%, 95% or 99% sequence identity thereto: SEQ. ID NOS. 3 to 16, 18, 20 to 33, 35 or 37 to 39.

In some embodiments of the present invention there is provided a polynucleotide comprising at least 75% of the ten nucleotides at the 3' end of one of the following primer sequences, or a sequence complementary thereto: SEQ. ID NOS. 3 to 16, 18, 20 to 33, 35 or 37 to 39.

Conveniently, the polynucleotide is less than 100 nucleotides long, preferably less than 80 nucleotides long, more preferably less than 60 nucleotides long, more preferably less than 40 nucleotides, more preferably less than 30 nucleotides long.

Advantageously, the polynucleotide further comprises a quencher group and a fluorophore group.

Conveniently, the quencher group and the fluorophore group are separated by a nucleotide tail sequence comprising first and second regions, the nucleotides of the first region being complementary to but in reverse order from the nucleotides of the second region, such that hybridisation of the first region to the second group results in the quencher group to be sufficiently close to the fluorophore group to quench the fluorophore group.

Preferably the tail sequence further comprises a third region having a sequence complementary to a region of the PIK3CA gene.

Advantageously, the polynucleotide comprises at least the six nucleotides at the 3' end of SEQ. ID NO. 18 and the tail sequence comprises SEQ. ID NO. 17.

Alternatively, the polynucleotide comprises at least the final nucleotides at the 3' end of SEQ. ID NO. 35 and the tail sequence comprises SEQ. ID NO. 34.

Alternatively, the polynucleotide comprises at least the final nucleotides at the 3' end of SEQ. ID NO. 39 and the tail sequence comprises SEQ. ID NO. 38.

Conveniently, the quencher group comprises Dabcyl.

Preferably the fluorophore comprises Hex, Fam or Rox.

According to another aspect of the present invention, there is provided a kit comprising at least two of the polynucleotides of the invention.

Advantageously, the kit comprises a polynucleotide comprising SEQ ID NO. 18 and a polynucleotide comprising any one of SEQ ID NOS. 3 to 16; or a polynucleotide comprising SEQ ID NO. 35 and a polynucleotide comprising any one of SEQ ID NOS. 20 to 33; or a polynucleotide comprising SEQ ID NO. 39 and a polynucleotide comprising SEQ ID NO. 37.

Conveniently, the kit further comprises nucleotide triphosphates, a polymerisation enzyme and/or a buffer solution.

According to a further aspect of the present invention, there is provided the use of a polynucleotide or a kit of the invention; or a polynucleotide comprising four or five of the six nucleotides at the 3' end of SEQ. ID NOS. 3 to 16, 18, 20 to 33 or 35 or sequences complementary thereto for detecting a mutation in a nucleic acid sample containing at least a fragment of the PIK3CA gene.

Advantageously, the fragment of the PIK3CA gene in the nucleic acid sample is at least 10 nucleotides long, preferably 20 nucleotides long, more preferably 30 nucleotides long and more preferably 40 nucleotides long, According to another aspect of the present invention, there is provided a method of detecting the presence or absence of a mutation in the PIK3CA gene comprising the steps of:

a) mixing a nucleic add sample comprising at least a fragment of the PIK3CA gene with a polynucleotide comprising at least the six nucleotides at the 3' end of one of the following primer sequences, or a sequence complementary thereto: SEQ ID NOS. 3 to 16 or 20 to 33; and b) detecting hybridisation of the polynucleotide to the nucleic acid sample wherein hybridisation indicates the presence of a mutation.

Conveniently, the polynucleotide comprises one of the following primer sequences: SEQ ID NGS. 3 to 16 or 20 to 33.

Preferably, the method further comprises the step of, prior to step a), amplifying the number of copies of the fragment of the PIK3CA gene using thermal cycling nucleic acid amplification, preferably PGR.

Advantageously, step b) comprises carrying out DNA polymerisation using the polynucleotide as a first primer and detecting the extension product of polymerisation.

Conveniently, step b) comprises the step of mixing the nucleic acid sample and the polynucleotide with a second primer which corresponds to a region of the fragment of the PIK3CA sequence downstream of the region to which the polynucleotide is complementary and carrying out PCR on the mixture.

Preferably, the second primer comprises: SEQ. ID NO. 18 and the polynucleotide comprises at least four or five of the six nucleotides at the 3' end of SEQ. ID NOS. 3 to 16; or the second primer comprises SEQ. ID NO. 35 and the polynucleotide comprises at least four or five of the six nucleotides at the 3' end of SEQ. ID NOS. 20 to 33.

Alternatively, the method further comprises the step of carrying out PCR on the sample using control primers and comparing the amplification of the P1K3CA gene with amplification using the polynucleotide and the second primer.

Advantageously, the control primers comprise SEQ ID NOS. 37 and 39.

Conveniently, the polynucleotide comprise a quencher group and a fluorophore group and wherein step b) comprises exposing the mixture to light of a wavelength to which the fluorophore is responsive in the absence of the quencher group and detecting light at the wavelength emitted by the fluorophore group in the absence of the quencher group.

It is preferred that the PIK3CA gene is the sequence available as GenBank accession no, NM_006218 version no. NM_006218.2 GI:54792081 which is incorporated herein by reference.

Where reference is made in the specification to "at least four or five of the six nucleotides at the 3' end" of a reference sequence, this means that, of the six nucleotides in the reference sequence, either one or two of the nucleotides may be missing or replaced with a different nucleotide. Of course, in some embodiments, the sequence comprises all six of the nucleotides of the reference sequence.

In this specification, "ARMS" is the amplification refractory mutation system disclosed in, for example, EP-A-0332435.

Where reference in this specification is made to a percentage of a polynucleotide compared with a reference polynucleotide, this can be determined by algorithms known in the art.

For example the percentage identity between two sequences can be determined using the BLASTP algorithm version 2.2.2 (Altschul, Stephen F., Thomas L. Madden, Alejandro A. Schäffer, Jinghui Zhang, Zheng Zhang, Webb Miller, and David J. Lipman (1997), "Gapped BLAST and PSSI-BLAST: a new generation of protein database search programs", Nucleic Acids Res. 25:3389-3402) using default parameters.

BRIEF DESCRIPTION OF DRAWINGS

FIG. 1 shows the results of carrying out Scorpions detection and sequencing on samples containing mutant PIK3CA gene.

DETAILED DESCRIPTION

Embodiments of the present invention provide polynucleotide primers that can be used in assays for the detection of mutations of the PIK3CA gene in a sample containing nucleic acids.

In specific embodiments, the polynucleotide primers are forward and reverse primers that hybridise with the PIK3CA gene to enable a PCR amplification reaction to take place. Thus the forward primer hybridises upstream of and to the opposite strand from the reverse primer and the forward and reverse primers together define an amplicon sequence which is amplified during PCR. The sequence of the forward primer is selected such that it is not complementary to the wild type sequence but is capable of hybridising with a mutant PIK3CA sequence.

In order to detect the presence the mutant PIK3CA gene in the sample, the primers are mixed with the sample. The necessary agents for PCR (appropriate nucleotide triphosphates, DNA polymerase enzyme and a buffer solution) are then added to the sample and PCR is carried out, if the sample contains the mutant sequence to which the forward primer is able to hybridise then the amplicon is amplified during PCR and the presence of the mutant sequence in the sample is thus indicated. If the sample does not contain the mutant sequence then the forward primer binds to the PIK3CA sequence with low efficiency and so there is little or no amplification of the amplicon sequence.

In order to detect the mutation E542K, the forward primer sequence may be one of SEQ ID NOS. 3 to 9, preferably SEQ ID NO. 5. In order to detect the mutation E545K, the forward primer sequence may be one of SEQ ID NOS. 10 to 16, preferably SEQ ID NO. 14. In order to detect the mutation H1047R, the forward primer sequence may be one of SEQ ID NOS. 20 to 26, preferably 21. In order to detect the mutation H1047L, the forward primer sequence may be one of SEQ ID NOS. 27 to 33, preferably 28. However, it is to be appreciated that the precise sequence of the forward primer need not be identical to these sequences, provided that the forward primer hybridises to the mutant sequence more readily than to the wild type sequence. In the sequences set out above, it is the final six nucleotides (i.e. the nucleotides at the 3' end) of the primers that provide the binding specificity so these nucleotides must be identical to the given sequence.

In order to detect the presence of the amplicons formed in the sample, the reverse primer is a so called "Scorpions" primer in embodiments of the present invention. Details of Scorpions primers are provided in WO-A-99/066071 which is incorporated herein by reference. A Scorpions primer comprises a primer sequence complementary to a first target sequence of a gene (in this invention PIK3CA) and a tail sequence comprises a probe sequence flanked by two mutually complementary sequences. A DNA polymerase blocking moiety (such as a hexethylene glycol (HEG) monomer) is provided between the primer sequence and the tail sequence. A fluorophore group is provided at one end of the tail sequence and a quencher group is provided at the other end of the tail sequence. In use, the primer sequence of the Scorpions primer acts as a reverse primer during PCR in the normal way and thus the entire Scorpions primer, including the tail sequence, becomes incorporated into each amplicon. The DNA polymerase blocking moiety prevents duplication of the tail sequence. Thus the mutually complementary sequences in the tail sequence have the tendency to hybridise with each other, bringing the fluorophore group and the quencher group into proximity and preventing emission from the fluorophore group. However, if the amplicon contains a second target sequence complementary to the probe sequence, the probe sequence preferentially binds to the second target sequence, separating the mutually complementary sequences. This results in the fluorophore group and the quencher group being spatially distanced such that the fluorophore group emits light of one wavelength in response to incident light of another wavelength. Accordingly, the Scorpions primer enables easy detection of amplicons and moreover, avoids false positive results (caused by primer dinners, for example) because a signal is only generated when the amplicon contains the second target sequence.

The fluorophore group may be Hex (4,7,2',4',5',7'-hexachloro-(3',6'-dipivaloylfluoresceinyl)-6-carboxamido-hexyl]-1-O-(2-cyanoethyl)-(N,N-diisopropyl)-phosphoramidite), Fam ([(3',6'-dipivaloylfluoresceinyl)-6-carboxamidohexyl]-1-O-(2-cyanoethyl)-(N,N-disopropyl)-phosphoramidite) or Rox (5,6,-Carboxy-X-Rhodamine). The quencher group may be Dabcyl (5'-Dimethoxytrityloxy-5-[(N-4'-carboxy-4-(dimethyiamino)-azobenzene)-aminohexyl-3-acrylimido]-2'-deoxyUridine-3'-[(2-cyanoethyl)-(N,N-diisopropyl)]-phosphoramidite).

In embodiments of the present invention, a Scorpions primer is provided for detection of the E542K and E546K mutations wherein the primer sequence is SEQ ID NO. 18 and the probe sequence is SEQ ID NO. 17. A Scorpions primer is provided for detection of the H1047R and the H1047L mutations wherein the primer sequence is SEQ ID NO. 35 and the probe sequence is SEQ ID NO. 34.

It is to be appreciated, however, that the use of Scorpions primers is not essential to the invention and other methods of detecting the synthesis of amplicons may be employed such as TaqMan™ product detection, as described in U.S. Pat. No. 5,487,972 and U.S. Pat. No. 5,210,015.

In some embodiments, a control assay is also carried out to detect the overall concentration of the PIK3CA gene in the sample. This is achieved by carrying out a separate PCR reaction with control forward and reverse primers which define an amplicon in another region of the PIK3CA gene. It is preferred that the forward primer is SEQ ID NO. 37 and the reverse primer is a Scorpions primer wherein the primer sequence is SEQ ID NO. 39 and the probe sequence is SEQ ID NO. 38. The number of PCR cycles required to generate a threshold number of control amplicons is then compared with the number of PCR cycles required to generate the threshold number of amplicons containing the mutant sequence in order to assess the proportion of mutant copies of the PIK3CA gene in the sample. Such control assays are generally carried out separately from the test assays.

The PCR assays are preferably carried out as multiplexed real time PCR assays.

The test sample of nucleic acid is conveniently a sample of blood, faeces, sputum, colonic lavage, bronchial lavage or other body fluid, or tissue obtained from an individual. The individual is conveniently human, preferably *Homo sapiens*. It will be appreciated that the test sample may equally be a nucleic acid sequence corresponding to the sequence in the test sample. That is to say that all or a part of the region in the sample nucleic acid may firstly be amplified using any convenient technique such as thermal cycling nucleic acid amplification, in particular PCR, or whole genome amplification (WGA) before use in the method of the invention.

Any convenient enzyme for polymerisation may be used provided that it does not affect the ability of the DNA polymerase to discriminate between normal and mutant template sequences to any significant extent. Examples of convenient enzymes include thermostable enzymes which have no significant 3'-5' exonuclease activity, for example Taq DNA polymerase, particularly "Ampli Taq Gold™ DNA polymerase (PE Applied Biosystems), Stoffel fragment, or other appropriately N-terminal deleted modifications of Taq or Tth (*Thermus thermophilus*) DNA polymerases.

In further embodiments of the present invention, there are provided kits comprising one or more polynucleotides of the invention and the nucleotide triphosphates, DNA polymerase enzyme and buffer solution required to carry out a PCR reaction. Preferred kits comprise forward and reverse primers for detection of a specific mutation and forward and reverse control primers.

EXAMPLES

Materials and Methods

Primers were designed against the 4 most common mutations in the PIK3CA gene (Accession Number: NM_006218). ARMS primers were designed to detect 2 mutations in exon 20: H1047R and H1047L; and 2 mutations in exon 9: E452K and E454K. A control primer was designed to cDNA position 2450 in the PIK3CA gene.

Scorpions were also designed. To allow multiplexing of a number of assays in each reaction the three scorpion primers were labelled with different fluorophores.

Primer Designs

A number of ARMS primers were designed specific for each target region. The target region for the E542K and E545K mutations are shown below as SEQ ID NOS. 1 and 2 respectively (the mutant bases are shown in brackets with the normal variant first). The forward primers to the mutations are also shown below (SEQ ID NOS. 3 to 16). To enhance the specificity of these reactions, additional primer mismatches close to the 3'-terminus were used (shown underlined in the primer sequences). The optimal primers (E542K-2 and E545K-4) were used for the experiments described. The Scorpions primer usable with the primer sequences is shown as SEQ ID NOS. 17 and 18. Regions of correspondence between the Scorpions primer and the target regions are shown in identical highlighting or underlining.

Exon 9 Region (SEQ ID NO. 1)
AACAGAGAATCTCCATTTTAGCACTTACCTGTGACTCCATAGAAAAT<u>CTTTCTCC</u>

<u>TGCTCAGTGATTT</u>(C/T)AGAGAGAGGAT<u>CTCGTGTAGAAATTGCTTTGAGCTGTT</u>

```
CTTTGTCATTTTCCCTTAATTCATTGTCTCTAGCTAGTCTGTTACTCTGTAAAATA
AAATAATATCTTATATA
                                                    (SEQ ID NO. 2)
AACAGAGAATCTCCATTTTAGCACTTACCTGTGACTCCATAGAAAATCTTTCTCC
TGCT(C/T)AGTGATTTCAGAGAGAGGATCTCGTGTAGAAATTGCTTTGAGCTGTT
CTTTGTCATTTTCCCTTAATTGATTGTCTCTAGCTAGTCTGTTACTCTGTAAAATA
AAATAATATCTTATATA
```

| Mutation | Primer Sequence | SEQ ID NO. |
|---|---|---|
| E542K-0 | 5'-CTTTCTCCTGCTCAGTGATTTT-3' | 3 |
| E542K-1 | 5'-CTTTCTCCTGCTCAGTGATTAT-3' | 4 |
| E542K-2 | 5'-CTTTCTCCTGCTCAGTGATTCT-3' | 5 |
| E542K-3 | 5'-CTTTCTCCTGCTCAGTGATTGT-3' | 6 |
| E542K-4 | 5'-CTTTCTCCTGCTCAGTGATATT-3' | 7 |
| E542K-5 | 5'-CTTTCTCCTGCTCAGTGATCTT-3' | 8 |
| E542K-6 | 5'-CTTTCTCCTGCTCAGTGATGTT-3' | 9 |
| E545K-0 | 5'-ACTCCATAGAAAATCTTTCTCCTGCTT-3' | 10 |
| E545K-1 | 5'-ACTCCATAGAAAATCTTTCTCCTGCAT-3' | 11 |
| E545K-2 | 5'-ACTCCATAGAAAATCTTTCTCCTGCCT-3' | 12 |
| E545K-3 | 5'-ACTCCATAGAAAATCTTTCTCCTGCGT-3' | 13 |
| E545K-4 | 5'-ACTCCATAGAAAATCTTTCTCCTGATT-3' | 14 |
| E545K-5 | 5'-ACTCCATAGAAAATCTTTCTCCTGGTT-3' | 15 |
| E545K-6 | 5'-ACTCCATAGAAAATCTTTCTCCTGTTT-3' | 16 |
| Exon 9 scorpion | Hex-CGCGCTCGTGTAGAAATTGCTTTGAGCGCG-que-heg-CAATGAATTAAGGGAAAATGAGA | 17 and 18 |

Exon 20 Region

The target region for the H1047R and H1047L mutations are shown below as SEQ ID NO. 19 (the mutant bases are shown in brackets with the normal variant first). The forward primers to the mutations are also shown below (SEQ ID NOS. 20 to 33). To enhance the specificity of these reactions, additional primer mismatches close to the 3'-terminus were used (shown underlined in the primer sequences). The optimal primers (H1047R-1 and H1047L-1) were used for the experiments described. The Scorpions primer usable with the primer sequences is shown as SEQ ID NOS. 34 and 35. Regions of correspondence between the Scorpions primer and the target regions are shown in identical highlighting or underlining.

```
                                                    (SEQ ID NO. 19)
AGTGCAGTGTGGAATCCAGAGTGAGCTTTCATTTTCTCAGTTATCTTTTCAGTTC
AATGCATGCTGTTTAATTGTGTGGAAGATCCAATCCATTTTGTTGTCCAGCCAC
CATGA(T/C/A)GTGCATCATTCATTTGTTTCATGAAATACTCCAAAGCCTCTTGCTC
AGTTTTATCTAAGGCTAGGGTCTTTCGAATGTATGCAATGTCATCAAAAGATTGT
AGTTCTGGCATTCCAGAGCCAAGCATCATTGAGAAAAGATTTATGAAGAGATTG
GCATGCTGTCGAATAGCTAGATAGCCTT
```

| Mutation | Primer Sequence | SEQ ID NO. |
|---|---|---|
| H1047R-0 | 5'-TGTTGTCCAGCCACCATGAC-3' | 20 |
| H1047R-1 | 5'-TGTTGTCCAGCCACCATGCC-3' | 21 |
| H1047R-2 | 5'-TGTTGTCCAGCCACCATGGC-3' | 22 |

-continued

| | | |
|---|---|---|
| H1047R-3 | 5'-TGTTGTCCAGCCACCATGTC-3' | 23 |
| H1047R-4 | 5'-TGTTGTCCAGCCACCATAAC-3' | 24 |
| H1047R-5 | 5'-TGTTGTCCAGCCACCATCAC-3' | 25 |
| H1047R-6 | 5'-TGTTGTCCAGCCACCATTAC-3' | 26 |
| H1047L-0 | 5'-TGTTGTCCAGCCACCATGAA-3' | 27 |
| H1047L-1 | 5'-TGTTGTCCAGCCACCATGCA-3' | 28 |
| H1047L-2 | 5'-TGTTGTCCAGCCACCATGGA-3' | 29 |
| H1047L-3 | 5'-TGTTGTCCAGCCACCATGTA-3' | 30 |
| H1047L-4 | 5'-TGTTGTCCAGCCACCATAAA-3' | 31 |
| H1047L-5 | 5'-TGTTGTCCAGCCACCATCAA-3' | 32 |
| H1047L-6 | 5'-TGTTGTCCAGCCACCATTAA-3' | 33 |
| Exon 20 scorpion | Fam-CGCGGCATGAAATACTCCAAAGCCGCG-que-Heg-CCCTAGCCTTAGATAAAACTGAGCAA | 34 and 35 |

Control Primers

The control primers are shown below. Regions of correspondence between the Scorpions primer and the target regions are shown in identical highlighting or underlining.

(SEQ ID NO. 36)
AGGCTTGAAGAGTGTCGAATTATGTCCTCTGCAAAAAGGCCACTGTGGTTGAAT

TGGGAGAACCCAGACATCATGTCAGAGTTACTGTTTCAGAACAATGAGATCATC

TTTAAAAATGGGGATGG

| Mutation | Primer Sequence | SE ID NO. |
|---|---|---|
| Control Primer | 5'-AGATGATCTCATTCTGAAACAG-3' | 37 |
| Control scorpion | Rox-CCGGCCAATTCAACCACAGTGGCCGG-Que-heg-GGCTTGAAGAGTGTCGAATTA | 38 and 39 |

All primers were synthesised and supplied by Invitrogen. PCR Buffer, Taq and Magnesium were supplied by Eurogentec and dNTPS were purchased from Abgene Ltd. Scorpions were synthesised and supplied by ATDBio.

Assays were multiplexed into 2 reactions containing a control assay and 2 ARMS assays (1× exon 9 and 1× exon 20). Assays were performed in 25 ul reaction volume containing 1×PCR Buffer, 4.0 mM MgCl$_2$, 200 uM dNTP mix, 0.25 uM of each primer (control primer and 2 ARMS primers) and 0.25 uM of each scorpion (control scorpion (SEQ ID NOS. 38 and 39), exon 20 scorpion (SEQ ID NOS. 34 and 35) and exon 9 scorpion (SEQ ID NOS. 17 and 18)). 2.5 ul of DNA template was added to each reaction. The H1047R and E542K primers were multiplexed with 2.5 unit Taq polymerase per reaction. The H1047L and E545K primers were multiplexed with 3.0 unit Taq polymerase per reaction. The E542K primer used was E542K-2 (SEQ ID NO. 5). The E545K primer used was E545K-4 (SEQ ID NO. 14). The H1047R primer used was H1047R-1 (SEQ ID HO. 21). The H1047L primer used was H1047L-1 (SEQ ID NO. 28).

In all cases the reactions were amplified on a Stratagene Mx3000P under the following conditions: 95° C. for 10 minutes, followed by 45 cycles of 90° C. for 30 seconds and 60° C. for 1 minute.

DNA cassettes harbouring point mutations to use as positive controls were constructed based on a method described by Higuchi et al[2]. In brief, corresponding outer and mutamer primers were used to generate half cassettes with complementary ends, each half cassette containing a mutant base. These PCR products were mixed and amplified with inner nested primers. Self priming of the complementary half cassettes and subsequent amplification created a final product with a mutated base. Products were sequenced to ensure the correct sequence had been created. This process was repeated for each mutation of interest. The DNA cassette was mixed with an equal amount of genomic DNA to create a 100% positive control.

Example 1

To determine the specificity of the reactions and the primers each assay was performed with 5-50 ng of genomic DNA per reaction to assess breakthrough signal caused by extension of mismatched primer. For each reaction a ΔCt value (control Ct-mutation Ct) was defined (Ct=threshold cycle). The reactions were performed six times for each DNA concentration and repeated in triplicate on separate occasions to define a cut off ΔCt value below which any amplification can be said to be due to the presence of mutant sequence and not due to breakthrough signal. The cut off ΔCt value was determined to be 1 Ct below the lowest ΔCt value seen in all reactions for each assay. For H1047R and H1047L assays the cut off ΔCt was defined as 12, for the E542K assay the cut off ΔCt was 9 and for the E545K assay the cut off ΔCt was 8.

Example 2

To assess the sensitivity of the assay, 5 copies of mutant DNA were diluted in varying concentrations of genomic DNA to give final concentrations of 5, 2, 1, 0.5 and 0.1% mutant DNA to wild type. Table 1 illustrates the sensitivity of the 4 ARMS assays. The table shows the ΔCt values for reducing concentrations of mutant DNA within a background of wild type DNA. The predefined cut off ΔCts are illustrated in the final column. The exon 20 assays were able to defect 5 copies of mutant DNA when this comprised only 0.1% of the total DNA (within the previously defined cut off ΔCt). The exon 9 assays were able to detect 5 copies of DNA at 1% concentration with a ΔCt within the predefined cut off values (Table 1).

TABLE 1

| WT DNA/ reaction (copies) | MUT DNA/ reaction (copies) | Relative % of MUT alleles | ΔCt H1047L | ΔCt H1047R | ΔCt E542K | ΔCt E545K | CUT OFF ΔCt | |
|---|---|---|---|---|---|---|---|---|
| 100 | 5 | 5% | 5.9 | 4.3 | 5.1 | 5.8 | | |
| 250 | 5 | 2% | 7.2 | 6.7 | 7.2 | 6.4 | H1047L | 12 |
| 500 | 5 | 1% | 8.3 | 7.6 | 8.4 | 7.0 | H1047R | 12 |
| 1000 | 5 | 0.5% | 9.3 | 9.0 | 10.2 | 8.1 | E542K | 9 |
| 5000 | 5 | 0.1% | 11.5 | 10.5 | 12.1 | 10.1 | E545K | 8 |

Example 3

Admixtures of cell lines containing mutation H1047R (HCT-116) and E545K (MCF-7) were used to compare the relative sensitivities of the ARMS assays compared with sequencing. Both cell lines were heterozygous for the mutation. Sequencing was performed using primers and PCR cycling conditions as described by Samuels et al[1]. ARMS assays and sequencing were carried out at concentrations of the mutant gene of 100%, 50%, 30%, 10% and 1% of the total mixture. The results are shown in FIG. 1 in which the results under the heading "Scorpions" show the increase in amplicon copy number after successive rounds of PCR (results using control primers and mutant primers are shown as separate lines). Under the heading "DNA Sequencing" is shown the results of sequencing the reverse strand of the gene in the mixture. Sequencing was not able to detect the presence of H1047R mutant when present at less than 50% of the total mixture and was unable to detect the presence of E545K mutant when present at less then 30% of the total mixture. Assays using the primers of the invention, by contrast, were able to detect the presence of mutants at 1% concentration.

Example 4

This assay was applied to DNA extracted from fresh frozen tissue from a variety of tumour types that were assessed for the presence of PIK3CA mutations using the ARMS/Scorpion assay. In total DNA was available from 279 tumour samples. The assay reported mutations in 5 of 49 (10.2%) colorectal cancer samples, 19 of 49 (38.7%) breast cancer samples, 1 of 51 (1.9%) lung cancer samples, and 1 of 34 (2.9%) melanoma samples. No mutations were detected in 50 prostate or 46 ovarian cancer samples. Of the colorectal samples positive for PIK3CA mutations 3 were H1047R, 1 was H1047L and 1 was E542K; of the breast cancer samples positive for PIK3CA, 15 were H1047R, 1 was H1047L and 3 were E545K; both the mutations in the lung cancer sample and melanoma sample positive for PIK3CA mutations were H1047R. Sequencing identified only 14 of the total 26 (53%) mutations detected. Sequencing detected a mutation in one breast cancer specimen which the ARMS assay was not designed to detect (c.1634 A>G; p E545G). This is not a novel mutation and has been previously described in breast and colorectal cancers[3-5].

The incidence of PIK3CA mutations in the samples analysed was consistent with previous studies with the exception of ovarian cancer[1,3-9]. PIK3CA mutations have been previously described in ovarian cancers but it has been suggested that there may be an associated with endometriod and clear cell cancers[8,10]. All the ovarian cancers tested in this study were serous adenocarcinomas which may explain the absence of any PIK3CA mutations.

The ARMS assay identified significantly more mutations in the clinical samples than seen by direct sequencing. The cell line admixtures confirm that this assay is more sensitive than sequencing in detecting the PI3KCA mutations of interest. It is likely that the heterogeneity of clinical samples that will contain both tumour and normal tissue will mean that in some instances the incidence of mutation will be below that detectable by sequencing methods and as such the ARMS assay is more suitable for clinical application. The drawback is that only certain ARMS specific mutations will be detected. However in this series of 279 samples only a single mutation in exon 9 or 20 of the PI3KCA gene was detected that the ARMS assay was not designed to detect.

In summary, the examples show that the present invention provides a sensitive, high throughput assay for the detection of the 4 most common mutations in the PIK3CA gene. This assay may be applied to small amounts of DNA and can detect low levels of mutant PIK3CA within a sample.

REFERENCES

1. Samuels Y, Wang Z, Bardelli A, et al. High frequency of mutations of the PIK3CA gene in human cancers. Science 2004; 304(5670):554.
2. Higuchi R, Krummel B, Saiki R K, A general method of in vitro preparation and specific mutagenesis of DNA fragments: study of protein and DNA interactions. Nucleic Acids Res 1988; 16(15):7351-87.

3. Wu G, Xing M, Mambo E, et al. Somatic mutation and gain of copy number of PIK3CA in human breast cancer. Breast Cancer Res 2005; 7(5):R609-16.
4. Levine D A, Bogomolnly F, Yee C J, et al. Frequent mutation of the PIK3CA gene in ovarian and breast cancers. Clin Cancer Res 2005; 11(8); 2875-8.
5. Velho S, Oliveira C, Ferreira A, et al. The prevalence of PIK3CA mutations in gastric and colon cancer. Eur J Cancer 2005; 41(11): 1649-54.
6. Lee J W, Soung Y H, Kim S Y, et al. PIK3CA gene is frequently mutated in breast carcinomas and hepatocellular carcinomas. Oncogene 2005; 24(8): 1477-80.
7. Bachman K E, Argani P, Samuels Y, et al. The PIK3CA gene is mutated with high frequency in human breast cancers. Cancer Biol Ther 2004; 3(8):772-5.
8. Campbell I G, Russell S E, Choong D Y, et al. Mutation of the PIK3CA gene in ovarian and breast cancer. Cancer Res 2004; 64(21):7678-81.
9. Omholt K, Krockel D, Ringborg U, Hansson J. Mutations of PIK3CA are rare in cutaneous melanoma, Melanoma Res 2006; 16(2):197-200.
10. Wang Y, Helland A, Holm R, Kristensen G B, Borresen-Dale A L. PIK3CA mutations in advanced ovarian carcinomas. Hum Mutat 2005; 25(3):322.

SEQUENCE LISTING

```
<160> NUMBER OF SEQ ID NOS: 39

<210> SEQ ID NO 1
<211> LENGTH: 180
<212> TYPE: DNA
<213> ORGANISM: Artificial
<220> FEATURE:
<223> OTHER INFORMATION: E542K target region

<400> SEQUENCE: 1
aacagagaat ctccatttta gcacttacct gtgactccat agaaaatctt tctcctgctc    60
agtgatttya gagagaggat ctcgtgtaga aattgctttg agctgttctt tgtcattttc   120
ccttaattca ttgtctctag ctagtctgtt actctgtaaa ataaaataat atcttatata   180

<210> SEQ ID NO 2
<211> LENGTH: 180
<212> TYPE: DNA
<213> ORGANISM: Artificial
<220> FEATURE:
<223> OTHER INFORMATION: E545K target region

<400> SEQUENCE: 2
aacagagaat ctccatttta gcacttacct gtgactccat agaaaatctt tctcctgcty    60
agtgatttca gagagaggat ctcgtgtaga aattgctttg agctgttctt tgtcattttc   120
ccttaattca ttgtctctag ctagtctgtt actctgtaaa ataaaataat atcttatata   180

<210> SEQ ID NO 3
<211> LENGTH: 22
<212> TYPE: DNA
<213> ORGANISM: Artificial
<220> FEATURE:
<223> OTHER INFORMATION: E542K-0 fwd primer

<400> SEQUENCE: 3
ctttctcctg ctcagtgatt tt    22

<210> SEQ ID NO 4
<211> LENGTH: 22
<212> TYPE: DNA
<213> ORGANISM: Artificial
<220> FEATURE:
<223> OTHER INFORMATION: E542K-1 fwd primer

<400> SEQUENCE: 4
ctttctcctg ctcagtgatt at    22

<210> SEQ ID NO 5
<211> LENGTH: 22
<212> TYPE: DNA
<213> ORGANISM: Artificial
```

```
<220> FEATURE:
<223> OTHER INFORMATION: E542K-2 fwd primer

<400> SEQUENCE: 5
ctttctcctg ctcagtgatt ct                                              22

<210> SEQ ID NO 6
<211> LENGTH: 22
<212> TYPE: DNA
<213> ORGANISM: Artificial
<220> FEATURE:
<223> OTHER INFORMATION: E542K-3 fwd primer

<400> SEQUENCE: 6
ctttctcctg ctcagtgatt gt                                              22

<210> SEQ ID NO 7
<211> LENGTH: 22
<212> TYPE: DNA
<213> ORGANISM: Artificial
<220> FEATURE:
<223> OTHER INFORMATION: E542K-4 fwd primer

<400> SEQUENCE: 7
ctttctcctg ctcagtgata tt                                              22

<210> SEQ ID NO 8
<211> LENGTH: 22
<212> TYPE: DNA
<213> ORGANISM: Artificial
<220> FEATURE:
<223> OTHER INFORMATION: E542K-5 fwd primer

<400> SEQUENCE: 8
ctttctcctg ctcagtgatc tt                                              22

<210> SEQ ID NO 9
<211> LENGTH: 22
<212> TYPE: DNA
<213> ORGANISM: Artificial
<220> FEATURE:
<223> OTHER INFORMATION: E542K-6 fwd primer

<400> SEQUENCE: 9
ctttctcctg ctcagtgatg tt                                              22

<210> SEQ ID NO 10
<211> LENGTH: 27
<212> TYPE: DNA
<213> ORGANISM: Artificial
<220> FEATURE:
<223> OTHER INFORMATION: E545K-0 fwd primer

<400> SEQUENCE: 10
actccataga aaatctttct cctgctt                                         27

<210> SEQ ID NO 11
<211> LENGTH: 27
<212> TYPE: DNA
<213> ORGANISM: Artificial
<220> FEATURE:
<223> OTHER INFORMATION: E545K-1 fwd primer

<400> SEQUENCE: 11
actccataga aaatctttct cctgcat                                         27
```

```
<210> SEQ ID NO 12
<211> LENGTH: 27
<212> TYPE: DNA
<213> ORGANISM: Artificial
<220> FEATURE:
<223> OTHER INFORMATION: E545K-2 fwd primer

<400> SEQUENCE: 12
actccataga aaatctttct cctgcct                                          27

<210> SEQ ID NO 13
<211> LENGTH: 27
<212> TYPE: DNA
<213> ORGANISM: Artificial
<220> FEATURE:
<223> OTHER INFORMATION: E545K-3 fwd primer

<400> SEQUENCE: 13
actccataga aaatctttct cctgcgt                                          27

<210> SEQ ID NO 14
<211> LENGTH: 27
<212> TYPE: DNA
<213> ORGANISM: Artificial
<220> FEATURE:
<223> OTHER INFORMATION: E454K-4 fwd primer

<400> SEQUENCE: 14
actccataga aaatctttct cctgatt                                          27

<210> SEQ ID NO 15
<211> LENGTH: 27
<212> TYPE: DNA
<213> ORGANISM: Artificial
<220> FEATURE:
<223> OTHER INFORMATION: E545K-5 fwd primer

<400> SEQUENCE: 15
actccataga aaatctttct cctggtt                                          27

<210> SEQ ID NO 16
<211> LENGTH: 27
<212> TYPE: DNA
<213> ORGANISM: Artificial
<220> FEATURE:
<223> OTHER INFORMATION: E545K-6 fwd primer

<400> SEQUENCE: 16
actccataga aaatctttct cctgttt                                          27

<210> SEQ ID NO 17
<211> LENGTH: 30
<212> TYPE: DNA
<213> ORGANISM: Artificial
<220> FEATURE:
<223> OTHER INFORMATION: Exon 9 Scorpion

<400> SEQUENCE: 17
cgcgctcgtg tagaaattgc tttgagcgcg                                       30

<210> SEQ ID NO 18
<211> LENGTH: 23
<212> TYPE: DNA
<213> ORGANISM: Artificial
<220> FEATURE:
<223> OTHER INFORMATION: Exon 9 Scorpion 2
```

<400> SEQUENCE: 18
caatgaatta agggaaaatg aca                                              23

<210> SEQ ID NO 19
<211> LENGTH: 300
<212> TYPE: DNA
<213> ORGANISM: Artificial
<220> FEATURE:
<223> OTHER INFORMATION: H1047R and H1047L target regions

<400> SEQUENCE: 19
agtgcagtgt ggaatccaga gtgagctttc attttctcag ttatcttttc agttcaatgc      60
atgctgttta attgtgtgga agatccaatc cattttttgtt gtccagccac catgahgtgc    120
atcattcatt tgtttcatga aatactccaa agcctcttgc tcagttttat ctaaggctag    180
ggtctttcga atgtatgcaa tgtcatcaaa agattgtagt tctggcattc cagagccaag    240
catcattgag aaaagattta tgaagagatt ggcatgctgt cgaatagcta gataagcctt    300

<210> SEQ ID NO 20
<211> LENGTH: 20
<212> TYPE: DNA
<213> ORGANISM: Artificial
<220> FEATURE:
<223> OTHER INFORMATION: H1047R-0 fwd primer

<400> SEQUENCE: 20
tgttgtccag ccaccatgac                                                  20

<210> SEQ ID NO 21
<211> LENGTH: 20
<212> TYPE: DNA
<213> ORGANISM: Artificial
<220> FEATURE:
<223> OTHER INFORMATION: H1047R-1 fwd primer

<400> SEQUENCE: 21
tgttgtccag ccaccatgcc                                                  20

<210> SEQ ID NO 22
<211> LENGTH: 20
<212> TYPE: DNA
<213> ORGANISM: Artificial
<220> FEATURE:
<223> OTHER INFORMATION: H1047R-2 fwd primer

<400> SEQUENCE: 22
tgttgtccag ccaccatggc                                                  20

<210> SEQ ID NO 23
<211> LENGTH: 20
<212> TYPE: DNA
<213> ORGANISM: Artificial
<220> FEATURE:
<223> OTHER INFORMATION: H1047R-3 fwd primer

<400> SEQUENCE: 23
tgttgtccag ccaccatgtc                                                  20

<210> SEQ ID NO 24
<211> LENGTH: 20
<212> TYPE: DNA
<213> ORGANISM: Artificial
<220> FEATURE:

<223> OTHER INFORMATION: H1047R-4 fwd primer

<400> SEQUENCE: 24
tgttgtccag ccaccataac 20

<210> SEQ ID NO 25
<211> LENGTH: 20
<212> TYPE: DNA
<213> ORGANISM: Artificial
<220> FEATURE:
<223> OTHER INFORMATION: H1047R-5 fwd primer

<400> SEQUENCE: 25
tgttgtccag ccaccatcac 20

<210> SEQ ID NO 26
<211> LENGTH: 20
<212> TYPE: DNA
<213> ORGANISM: Artificial
<220> FEATURE:
<223> OTHER INFORMATION: H1047R-6 fwd primer

<400> SEQUENCE: 26
tgttgtccag ccaccattac 20

<210> SEQ ID NO 27
<211> LENGTH: 20
<212> TYPE: DNA
<213> ORGANISM: Artificial
<220> FEATURE:
<223> OTHER INFORMATION: H1047L-0 fwd primer

<400> SEQUENCE: 27
tgttgtccag ccaccatgaa 20

<210> SEQ ID NO 28
<211> LENGTH: 20
<212> TYPE: DNA
<213> ORGANISM: Artificial
<220> FEATURE:
<223> OTHER INFORMATION: H1047L-1 fwd primer

<400> SEQUENCE: 28
tgttgtccag ccaccatgca 20

<210> SEQ ID NO 29
<211> LENGTH: 20
<212> TYPE: DNA
<213> ORGANISM: Artificial
<220> FEATURE:
<223> OTHER INFORMATION: H1047L-3 fwd primer

<400> SEQUENCE: 29
tgttgtccag ccaccatgga 20

<210> SEQ ID NO 30
<211> LENGTH: 20
<212> TYPE: DNA
<213> ORGANISM: Artificial
<220> FEATURE:
<223> OTHER INFORMATION: H1047-3 fwd primer

<400> SEQUENCE: 30
tgttgtccag ccaccatgta 20

-continued

```
<210> SEQ ID NO 31
<211> LENGTH: 20
<212> TYPE: DNA
<213> ORGANISM: Artificial
<220> FEATURE:
<223> OTHER INFORMATION: H1047L-4 fwd primer

<400> SEQUENCE: 31
tgttgtccag ccaccataaa                                               20

<210> SEQ ID NO 32
<211> LENGTH: 20
<212> TYPE: DNA
<213> ORGANISM: Artificial
<220> FEATURE:
<223> OTHER INFORMATION: H1047L-5 fwd primer

<400> SEQUENCE: 32
tgttgtccag ccaccatcaa                                               20

<210> SEQ ID NO 33
<211> LENGTH: 20
<212> TYPE: DNA
<213> ORGANISM: Artificial
<220> FEATURE:
<223> OTHER INFORMATION: H1047L-6 fwd primer

<400> SEQUENCE: 33
tgttgtccag ccaccattaa                                               20

<210> SEQ ID NO 34
<211> LENGTH: 27
<212> TYPE: DNA
<213> ORGANISM: Artificial
<220> FEATURE:
<223> OTHER INFORMATION: Exon 20 Scorpion

<400> SEQUENCE: 34
cgcggcatga aatactccaa agccgcg                                       27

<210> SEQ ID NO 35
<211> LENGTH: 26
<212> TYPE: DNA
<213> ORGANISM: Artificial
<220> FEATURE:
<223> OTHER INFORMATION: Exon 20 Scorpion 2

<400> SEQUENCE: 35
ccctagcctt agataaaact gagcaa                                        26

<210> SEQ ID NO 36
<211> LENGTH: 125
<212> TYPE: DNA
<213> ORGANISM: Artificial
<220> FEATURE:
<223> OTHER INFORMATION: Control target region

<400> SEQUENCE: 36
aggcttgaag agtgtcgaat tatgtcctct gcaaaaaggc cactgtggtt gaattgggag   60
aacccagaca tcatgtcaga gttactgttt cagaacaatg agatcatctt taaaaatggg  120
```

```
<210> SEQ ID NO 37
<211> LENGTH: 25
<212> TYPE: DNA
<213> ORGANISM: Artificial
<220> FEATURE:
<223> OTHER INFORMATION: Control primer

<400> SEQUENCE: 37
agatgatctc attgttctga aacag                                              25

<210> SEQ ID NO 38
<211> LENGTH: 26
<212> TYPE: DNA
<213> ORGANISM: Artificial
<220> FEATURE:
<223> OTHER INFORMATION: Control Scorpion

<400> SEQUENCE: 38
ccggccaatt caaccacagt ggccgg                                             26

<210> SEQ ID NO 39
<211> LENGTH: 21
<212> TYPE: DNA
<213> ORGANISM: Artificial
<220> FEATURE:
<223> OTHER INFORMATION: Control Scorpion 2

<400> SEQUENCE: 39
ggcttgaaga gtgtcgaatt a                                                  21
```

(preceding page continued: `gatgg` 125)

We claim:

1. A method of detecting a mutation in a nucleic acid sample containing at least a fragment of the phosphatidylinositol 3-kinase catalytic subunit A (PIK3CA) gene comprising:
   a) mixing the nucleic acid sample with a polynucleotide comprising a sequence corresponding to SEQ ID NO:21 to produce a mixture;
   b) amplifying copies of a fragment of a PIK3CA gene in the mixture using thermal cycling nucleic acid amplification to produce amplicons; and
   c) detecting hybridization of the polynucleotide to the nucleic acid sample wherein hybridization indicates the presence of the mutation in the PIK3CA gene.

2. The method of claim 1 further comprising, prior to a), amplifying the number of copies of the fragment of the PIK3CA gene using thermal cycling nucleic acid amplification.

3. The method according to claim 1, wherein the polynucleotide is less than 100 nucleotides long.

4. The method according to claim 1, wherein the polynucleotide further comprises a quencher group and a fluorophore group.

5. The method according to claim 4, wherein the quencher group and the fluorophore group are separated by a nucleotide tail sequence comprising first and second regions, the nucleotides of the first region being complementary to but in reverse order from the nucleotides of the second region, such that hybridization of the first region to the second group results in the quencher group to be sufficiently close to the fluorophore group to quench the fluorophore group.

6. The method according to claim 5, wherein the tail sequence further comprises a third region having sequence complementary to a region of the PIK3CA gene.

7. The method of claim 1, wherein the polynucleotide hybridizes to a H1047R mutant sequence of the PIK3CA gene but is not complementary to the wild type sequence.

8. A method of detecting the presence or absence of a mutation in the PIK3CA gene comprising:
   a) mixing a nucleic acid sample comprising at least a fragment of the PIK3CA gene with a polynucleotide comprising SEQ ID NO:21; and
   b) detecting hybridization of the polynucleotide to the nucleic acid sample wherein hybridization indicates the presence of a mutation.

9. The method according to claim 8 further comprising, prior to a), amplifying the number of copies of the fragment of the PIK3CA gene using thermal cycling nucleic acid amplification.

10. The method according to claim 8, wherein b) comprises carrying out DNA polymerisation using the polynucleotide as a first primer and detecting the extension product of polymerisation.

11. The method according to claim 10 wherein b) comprises the step of mixing the nucleic acid sample and the polynucleotide with a second primer which corresponds to a region of the fragment of the PIK3CA sequence downstream of the region to which the polynucleotide is complementary and carrying out PCR on the mixture.

12. The method according to claim 11 wherein the second primer comprises SEQ ID NO:35.

13. The method according to claim 11 further comprising carrying out PCR on the nucleic acid sample using control primers that bind to a different region of PIK3CA compared to the polynucleotide and second primer and comparing the control amplification of the PIK3CA gene with amplification using the polynucleotide and the second primer.

14. The method according to claim 13 wherein the control primers comprise SEQ ID NOS: 37 and 39.

15. The method according to claim 8 wherein the polynucleotide comprises a quencher group and a fluorophore group and wherein b) comprises exposing the mixture to light of a wavelength to which the fluorophore is responsive in the absence of the quencher group and detecting light at the wavelength emitted by the fluorophore group in the absence of the quencher group.

* * * * *